United States Patent [19]
Steffee

[11] Patent Number: 5,716,415
[45] Date of Patent: Feb. 10, 1998

[54] SPINAL IMPLANT

[75] Inventor: Arthur D. Steffee, Novelty, Ohio

[73] Assignee: AcroMed Corporation, Cleveland, Ohio

[21] Appl. No.: 612,674

[22] Filed: Mar. 8, 1996

Related U.S. Application Data

[63] Continuation of Ser. No. 287,096, Aug. 8, 1994, abandoned, which is a continuation-in-part of Ser. No. 130,288, Oct. 1, 1993, Pat. No. 5,443,514.

[51] Int. Cl.$^6$ ........................................ A61F 2/44
[52] U.S. Cl. ........................................ 623/17
[58] Field of Search ............... 623/16, 17; 606/61, 606/99

[56] References Cited

U.S. PATENT DOCUMENTS

| | | | |
|---|---|---|---|
| 4,566,466 | 1/1986 | Ripple et al. | 128/781 |
| 4,834,757 | 5/1989 | Brantigan | 623/17 |
| 5,122,130 | 6/1992 | Keller | 606/61 |
| 5,147,402 | 9/1992 | Bohler et al. | 623/16 |
| 5,192,327 | 3/1993 | Brantigan | 623/7 |
| 5,306,307 | 4/1994 | Senter et al. | 623/17 |
| 5,425,772 | 6/1995 | Brantigan | 623/17 |

FOREIGN PATENT DOCUMENTS

| | | |
|---|---|---|
| 1146301 | 5/1983 | Canada. |
| 0493698 | 12/1991 | European Pat. Off.. |
| 3505567 | 2/1985 | Germany. |
| 2104019 | 8/1990 | Japan. |
| 40411644 | 4/1992 | Japan ........ 623/17 |
| 1107854 | 8/1984 | U.S.S.R. ...... 623/17 |
| 8912431 | 12/1989 | WIPO. |
| 94017759 | 8/1994 | WIPO ......... 623/17 |
| 94 28824 | 12/1994 | WIPO ......... 623/17 |

*Primary Examiner*—Michael J. Milano
*Attorney, Agent, or Firm*—Tarolli, Sundheim, Covell, Tummino & Szabo

[57] ABSTRACT

A spinal implant for use in distracting and maintaining spinal disc height while promoting fusion of adjacent vertebrae of a spinal column includes first and second side surfaces extending substantially parallel to each other. Upper and lower surfaces for engaging the adjacent vertebrae extend between the first and second side surfaces and extend from a first end portion to a second end portion of the spinal implant. The spinal implant includes recesses located in the first and second side surfaces for receiving an instrument to rotate the spinal implant. A method of fusing together the adjacent vertebrae using the spinal implant includes removing at least a portion of the spinal disc between the adjacent vertebrae. The spinal implant is inserted between the adjacent vertebrae with the first and second parallel side surfaces facing the adjacent vertebrae. The spinal implant is rotated into a position in which the parallel side surfaces extend from one of the adjacent vertebrae to the other adjacent vertebrae and the upper and lower surfaces engage the adjacent vertebrae.

21 Claims, 5 Drawing Sheets

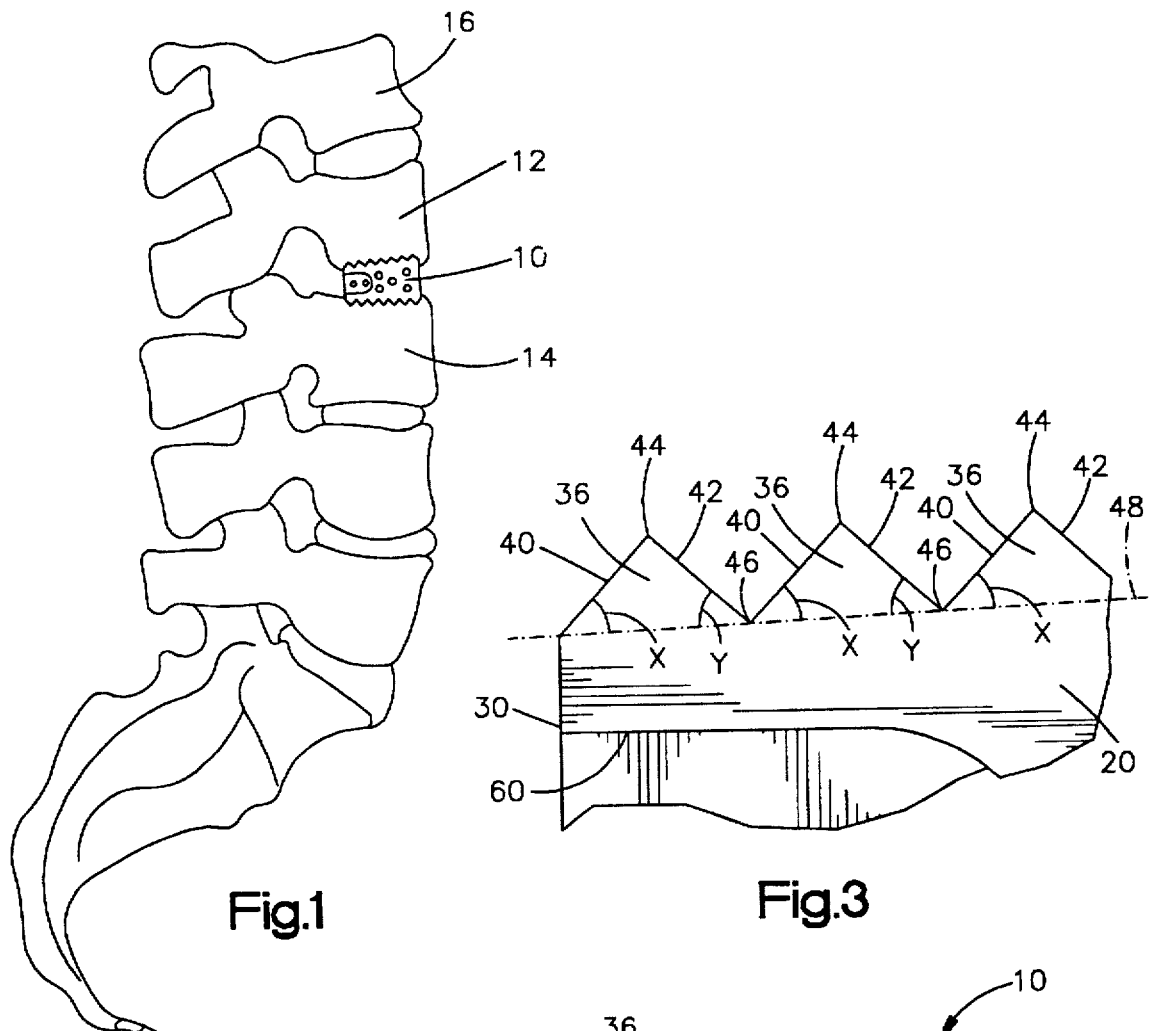
Fig.1
Fig.3
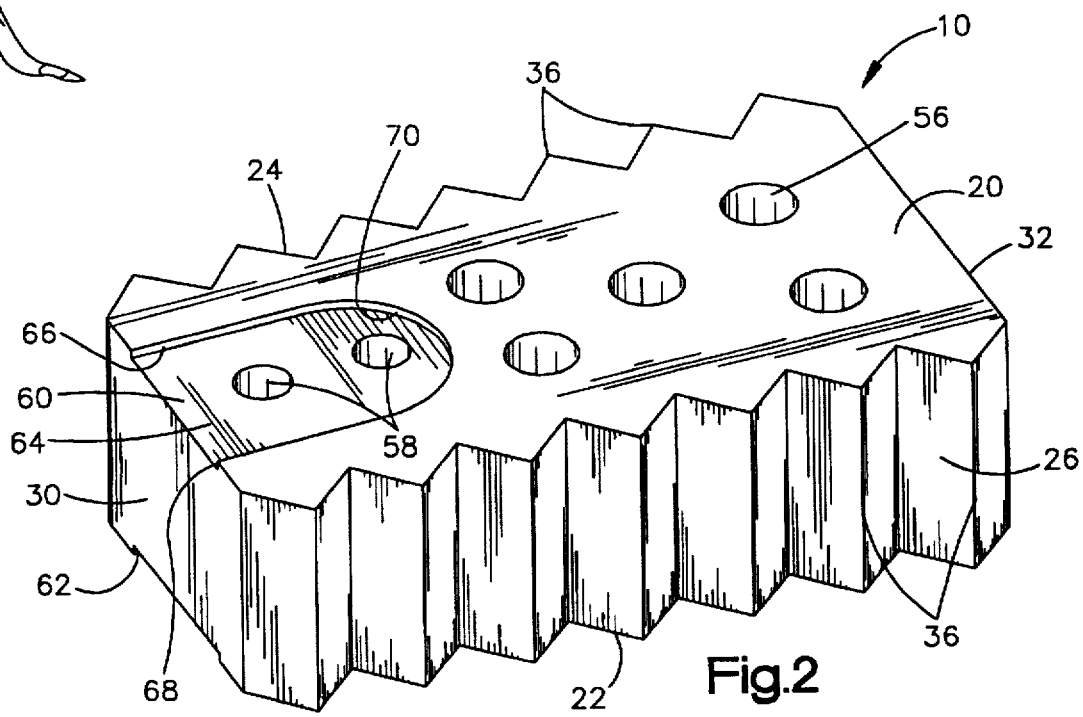
Fig.2

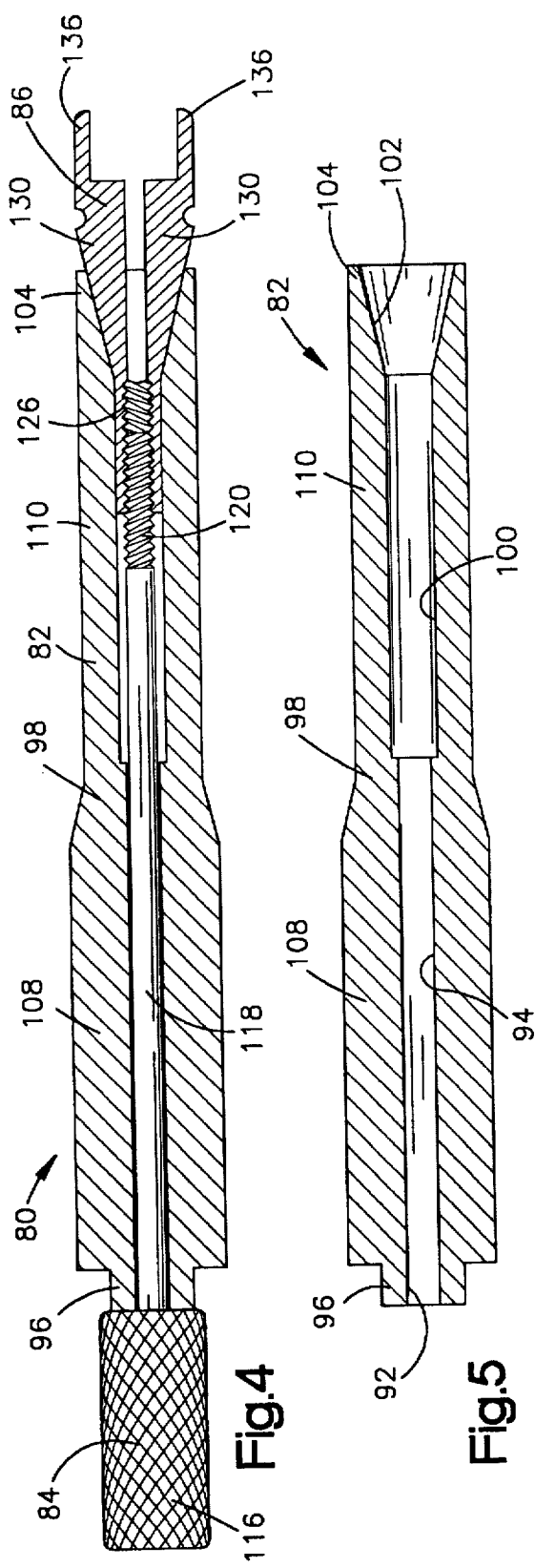
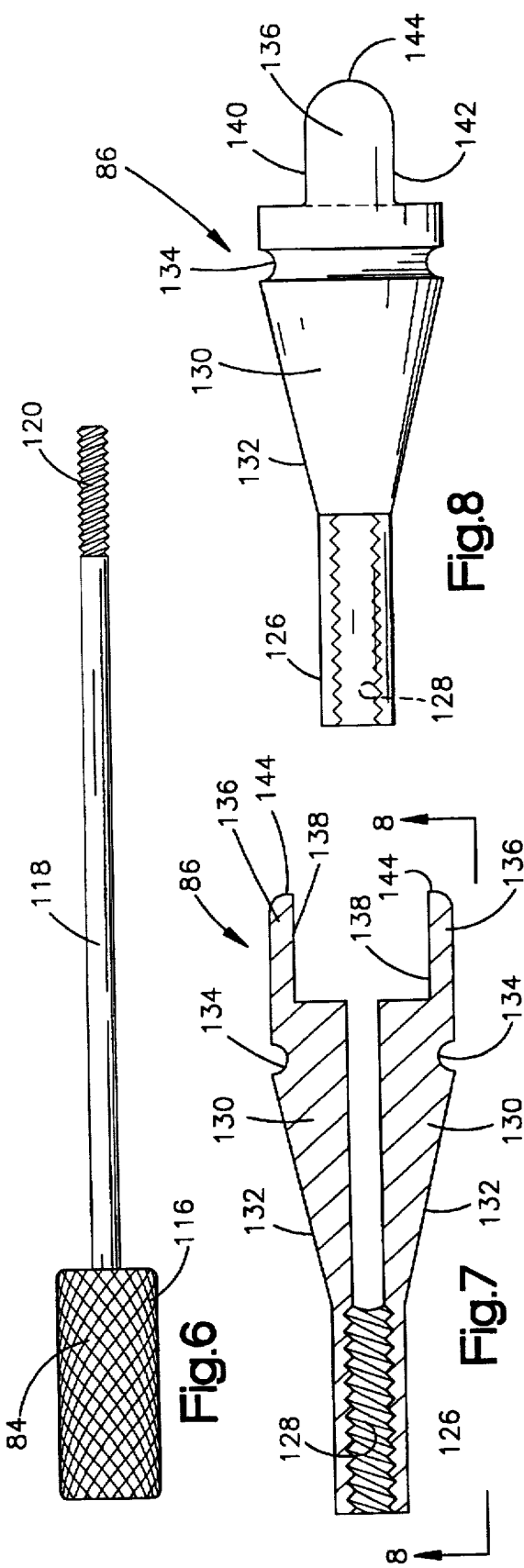

5,716,415

SPINAL IMPLANT

This application is a continuation of U.S. patent application Ser. No. 287,096, filed Aug. 8, 1994 and now abandoned, which is a continuation-in-part of U.S. application Ser. No. 130,288 filed Oct. 1, 1993, now U.S. Pat No. 5,443,514.

BACKGROUND OF THE INVENTION

The present invention relates to a spinal implant, and to a method of using the spinal implant to fuse together adjacent vertebrae of a spinal column.

A known spinal implant has a rectangular shape and a tapered end. The spinal implant includes nubs to grip adjacent vertebrae. The nubs have inclined faces that accommodate forward sliding movement of the spinal implant into channels cut in the adjacent vertebrae. This known spinal implant is described in U.S. Pat. No. 4,834,757. By cutting channels into the vertebrae for receiving the spinal implant, nerve roots are put at risk.

SUMMARY OF THE INVENTION

The present invention provides a new and improved spinal implant and method of using the spinal implant to fuse together adjacent vertebrae of a spinal column. The spinal implant of the present invention includes first and second side surfaces extending substantially parallel to each other. Upper and lower surface means for engaging the adjacent vertebrae extend between the first and second side surfaces and extend from a first end portion to a second end portion of the spinal implant. The spinal implant includes means engagable with a tool for rotating the spinal implant when the implant is located between the adjacent vertebrae.

The method of using the spinal implant to fuse together the adjacent vertebrae of a spinal column includes removing at least a portion of the spinal disc between the adjacent vertebrae. The spinal implant is inserted between the adjacent vertebrae with the first and second substantially parallel side surfaces facing the adjacent vertebrae. The spinal implant is rotated into a position in which the parallel side surfaces extend from one of the adjacent vertebrae to the other of the adjacent vertebrae and the upper and lower surface means engage the adjacent vertebrae. There are no channels cut in the adjacent vertebrae. Thus, the operation takes less time and lessens the risks to the patient.

BRIEF DESCRIPTION OF THE DRAWINGS

The foregoing and other features of the present invention will become more apparent to one skilled in the art upon reading the following description of the present invention with reference to the accompanying drawings, wherein:

FIG. 1 is an elevation view of a human spinal column having a first embodiment of a spinal implant in accordance with the present invention placed therein;

FIG. 2 is a perspective view of the spinal implant of FIG. 1;

FIG. 3 is an enlarged plan view looking at a portion of the spinal implant of FIG. 2 from the side;

FIG. 4 is a sectional view of an instrument for holding the spinal implant of FIG. 2 to facilitate inserting the spinal implant between adjacent vertebrae and rotating the spinal implant;

FIG. 5 is a sectional view of an intermediate portion of the instrument of FIG. 4;

FIG. 6 is a plan view of a handle of the instrument of FIG. 4;

FIG. 7 is a sectional view of a clamp portion of the instrument of FIG. 4;

FIG. 8 is a plan view of the clamp portion of FIG. 7 taken along the line 8—8 of FIG. 7;

DESCRIPTION OF A PREFERRED EMBODIMENT

Figure 9:
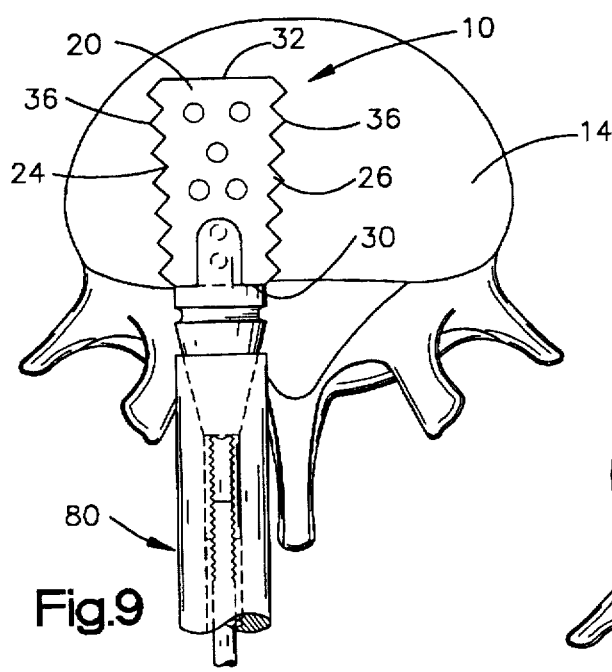
FIGS. 9–12 are views showing a method of inserting spinal implants in a side-by-side relationship between adjacent vertebrae.
Figure 10:
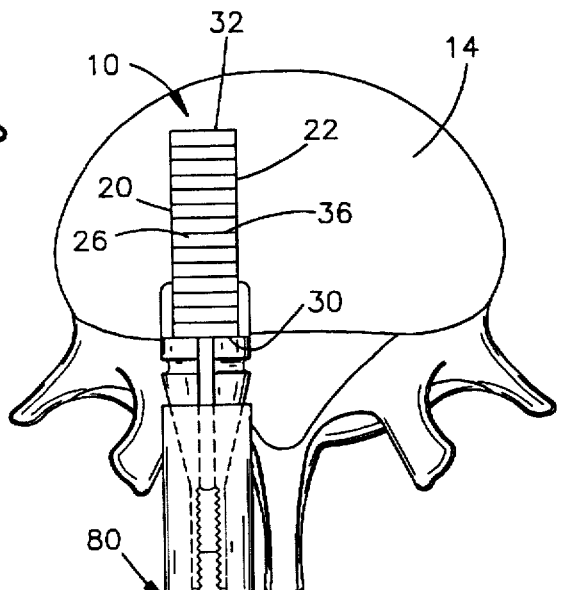

A first embodiment of a spinal implant of the present invention and method of inserting the spinal implant between adjacent vertebrae are shown in FIGS. 1–12.

One or several substantially rigid spinal implants 10 (one of which is shown in FIG. 1) are placed between adjacent vertebrae 12 and 14 of a spinal column 16 in a side-by-side relationship to fuse together the adjacent vertebrae. Preferably, the spinal implants 10 are made by injection molding a chopped carbon fiber reinforced polymer. However, the spinal implants 10 can be made of other suitable implantable materials such as stainless steel or titanium. Also, preferably, the ultimate tensile strength of the material used to make the spinal implants 10 is higher than 10,000 psi so that the spinal implants will prevent relative movement between the adjacent vertebrae 12 and 14 and will support the compressive load of the spinal column.

Each of the spinal implants 10 (FIG. 2) has parallel side surfaces 20 and 22. An upper surface 24 and a lower surface 26 for engaging the adjacent vertebrae 12 and 14 extend between the side surfaces 20 and 22. The upper and lower surfaces 24 and 26 adjacent a first end portion 30 of the spinal implant 10 are spaced apart by a first distance. The upper and lower surfaces 24 and 26 adjacent a second end portion 32 of the spinal implant 10 are spaced apart a second distance. The second distance is preferably greater than the first distance to give the spinal implant a wedge shape for use in portions of the spine with a lordotic curve. Although the spinal implant 10 is shown with a wedge shape for use in portions of the spine with a lordotic curve, the implant may have a wedge shape for use in portions of the spine with a kyphotic curve or may not be wedge shaped at all.

The upper and lower surfaces 24 and 26 include a plurality of triangular-shaped teeth 36 that extend from the side surface 20 to the side surface 22 for engaging the vertebrae 12 and 14. Each tooth 36 (FIG. 3) includes a surface 40 facing toward the end portion 30. A surface 42 of the tooth 36 faces the end portion 32 of the spinal implant 10. The surfaces 40 and 42 of the tooth 36 intersect each other to form an edge 44. The surfaces 40 and 42 of adjacent teeth 36 intersect to form edges 46. The edges 46 are parallel to each other and lie in a plane 48.

The surface 40 of the tooth 36 extends at an acute angle X to the plane 48. The surface 42 of the tooth 36 extends at an acute angle Y to the plane 48. Preferably, the angles X and Y are equal and have a value of 45° so that surfaces 40 and 42 extend perpendicular to each other. Therefore, the teeth 36 are not preferential. The teeth 36 prevent the spinal implant 10 from moving toward the anterior portion of the spinal column 16 as much as they prevent the spinal implant from moving toward the posterior portion of the spinal column 16. However, the angles X and Y may have different values as desired by a surgeon.

A plurality of openings 56 and 58 extend from the side surface 20 to the side surface 22 to provide for the flow of body fluids and bone growth from one side of the implant 10 to the other side of the implant. The openings 58 are located near the end portion 30 of the implant. The openings 56 and 58 extend perpendicular to the side surfaces 20 and 22. Preferably, there are five openings 56 and two openings 58 extending between the sides 20 and 22. The openings 56 have diameters larger than the diameters of the openings 58. The sizes, shapes, and positions of the openings 56 and 58 may be varied as desired by a surgeon. Although the openings 56 and 58 are shown extending perpendicular to the side surfaces 20 and 22, the openings 56 and 58 may extend at an acute angle to the side surfaces 20 and 22. Also, it is contemplated that the spinal implant 10 may include recesses in the side surfaces 20 and 22 for receiving autograft or allograft bone, bone proteins, bone substitute, or the like instead of or along with the openings 56 and 58.

The side surface 20 includes a recess 60 and the side surface 22 includes a recess 62. The openings 58 are located in the recesses 60 and 62. Each of the recesses 60 and 62 includes a planar bottom surface 64. The recesses 60 and 62 also include parallel side surfaces 66 and 68 extending perpendicular to the bottom surface 64 and from the end portion 30 of the spinal implant 10 toward the end portion 32. An arcuate side surface 70 extends between the parallel side surfaces 66 and 68. The recesses 60 and 62 may be located anywhere on the surfaces 20 and 22 depending on whether the implant 10 is going to be inserted posteriorly, anteriorly, or anterio-laterally. The recesses 60 and 62 in the side surfaces 20 and 22 are for receiving an instrument 80 (FIG. 4) that holds the spinal implant 10 to facilitate insertion of the spinal implant between the adjacent vertebrae 12 and 14 and rotation of the spinal implant once between the adjacent vertebrae.

Any instrument that firmly holds the implant and permits the implant to be rotated into position can be used. One such instrument 80 (FIG. 4) includes an intermediate portion 82 (FIG. 5), a handle 84 (FIG. 6) and a clamp portion 86 (FIGS. 7 and 8).

The intermediate portion 82 (FIG. 5) is generally cylindrical and includes an opening 92 extending along the axis of the intermediate portion. The opening 92 includes a first cylindrical portion 94 extending from an end portion 96 of the intermediate portion 82 to a central portion 98. A second cylindrical portion 100 of the opening 92 extends from the first cylindrical portion 94 to a tapered portion 102 of the opening 92. The second cylindrical portion 100 of the opening 92 has a diameter larger than the diameter of the first cylindrical portion 94. The tapered portion 102 of the opening 92 tapers from a small diameter adjacent the portion 100 to a larger diameter adjacent an end portion 104 of the intermediate portion 82.

The intermediate portion 82 includes a large outer diameter portion 108 that extends from the end portion 96 to the central portion 98. The portion 108 tapers from a large outer diameter to a small outer diameter portion 110 which extends from the portion 108 to the end portion 104. The outer surface of the portion 108 is preferably knurled to provide for easy gripping of the intermediate portion 82 by a surgeon. The end portion 96 has a diameter which is smaller than the portions 108 and 110.

The handle 84 (FIG. 6) has a large diameter knurled portion 116. A small diameter shaft 118 extends from the knurled portion 116. The shaft 118 has a threaded end 120 for threadably engaging the clamp portion 86.

The clamp portion 86 (FIGS. 7 and 8) includes a stem 126 with an internally threaded opening 128 for receiving the threaded end 120 of the handle 84. A pair of clamp halves 130 are spaced apart and extend from the stem 126. The clamp halves 130 have outwardly tapering surfaces 132. The surfaces 132 taper from the stem 126 to a groove 134.

The clamp halves 130 include extensions 136 which are received in the recesses 60 and 62 in the side surfaces 20 and 22 of the spinal implant 10. The extensions 136 include planar inner surfaces 138 (FIG. 7) for engaging the bottom planar surfaces 64 of the recesses 60 and 62. Parallel side surfaces 140 and 142 (FIG. 8) of the extensions 136 engage side surfaces 66 and 68 of the recesses 60 and 62 when the instrument 80 is used to hold the spinal implant 10. Arcuate side surface 144 for engaging the side surface 70 extends between the side surfaces 140 and 142.

The shaft 118 of the handle 84 extends into the opening 92 in the intermediate portion 82 and threadably engages the stem 126 of the clamp portion 86 (FIG. 4). As the handle 84 is threaded into the opening 128 of the clamp portion 86, the clamp portion is drawn into the opening 92 in the intermediate portion 82. The tapered surfaces 132 of the clamp halves 130 engage the tapered portion 102 of the opening 92. As the clamp portion 86 is drawn into the opening 92, the clamp halves 130 are forced toward each other by the tapered portion 102 of the opening 92 to clamp the spinal implant 10 between the extensions 136.

The method of placing the spinal implants 10 between the adjacent vertebrae 12 and 14 to fuse together the adjacent vertebrae will now be described. Most of the spinal disc located between the vertebrae 12 and 14 is removed. The facing surfaces of the vertebrae 12 and 14 are cleaned with a disc shaver and rongeurs. Preferably, an annulus of the spinal disc is left between the vertebrae 12 and 14.

The instrument 80 is used to hold a spinal implant 10. The spinal implant 10 is inserted posteriorly, anteriorly, or anterio-laterally as desired by a surgeon between the vertebrae 12 and 14 with the parallel side surfaces 20 and 22 facing the adjacent vertebrae 12 and 14. The implant 10 is shown being inserted posteriorly in FIG. 9. The spinal implant 10 is inserted so that the end portion 32 is near the anterior side of the spinal column 16 and the end portion 30 is near the posterior side of the spinal column. The spinal implant 10 is rotated 90° to the position shown in FIG. 10 so that the teeth 36 on the upper and lower surfaces 24 and 26 engage the vertebrae 12 and 14 and the side surfaces 20 and 22 extend from the vertebra 12 to the vertebra 14. The wedge shape of the spinal implant 10 alleviates the need to distract the posterior portion of the spine segment a large distance and then compress the posterior portion to achieve the required lordosis. The posterior portion only needs to be distracted to the desired interdiscal height.

Figure 11:
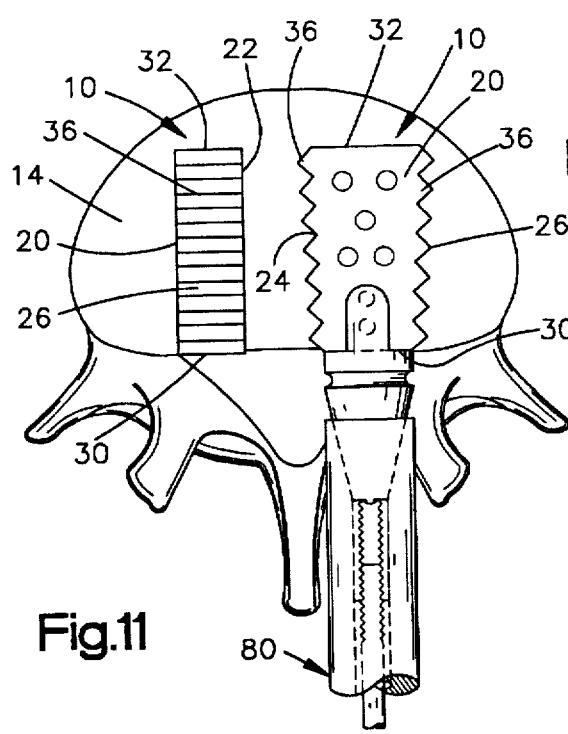
Figure 12:
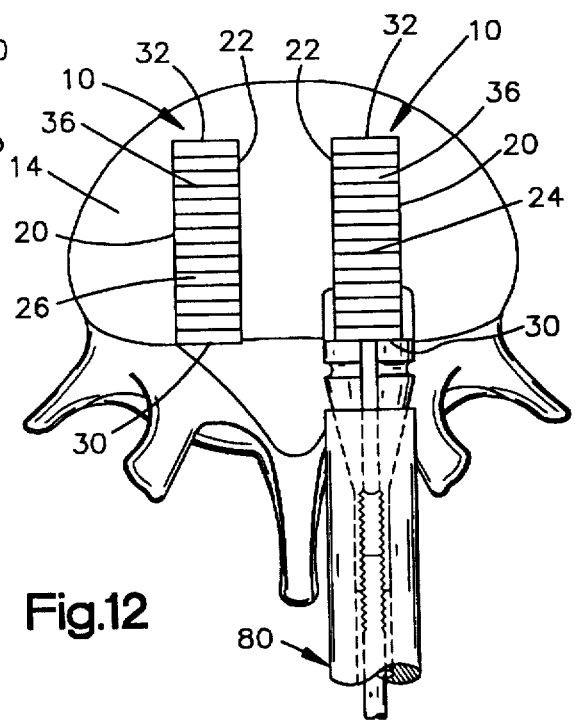

A second spinal implant 10 is inserted between the vertebrae 12 and 14 in a side-by-side relationship with the first spinal implant. The second spinal implant 10 is inserted in a similar manner as the first implant. The instrument 80 is used to hold the spinal implant 10. The spinal implant 10 is inserted with the parallel side surfaces 20 and 22 facing the vertebrae 12 and 14 (FIG. 11). The second spinal implant 10 is then rotated 90° to the position shown in FIG. 12 so that the teeth 36 of the upper and lower surfaces 24 and 26 engage the vertebrae 12 and 14.

The remaining space between the spinal implants 10 and the adjacent vertebrae 12 and 14 is packed with autograft or allograft bone, bone proteins, bone substitute, or the like. An apparatus for maintaining the vertebrae 12 and 14 in a desired spatial relationship such as that disclosed in U.S. Pat. No. 4,696,290 is attached to the spinal column 16 until the vertebrae 12 and 14 have completely fused together. The apparatus for maintaining the vertebrae 12 and 14 in the desired spatial relationship prevents the spinal implants 10 from moving out of position and the bone graft from falling out of the spaces between the spinal implants and the vertebrae 12 and 14.

In the embodiment of the invention illustrated in FIGS. 1–12, the spinal implant 10 has relatively small openings 56 and 58. In the embodiment of the invention illustrated in FIGS. 13 and 14, the spinal implant has a relatively large opening extending between side surfaces. Since the embodiment of the invention illustrated in FIGS. 13 and 14 is generally similar to the embodiment of the invention illustrated in FIGS. 1–12, similar numerals will be utilized to designate similar components, the suffix letter "a" being associated with the numerals of FIGS. 13 and 14 to avoid confusion.

Figure 13:
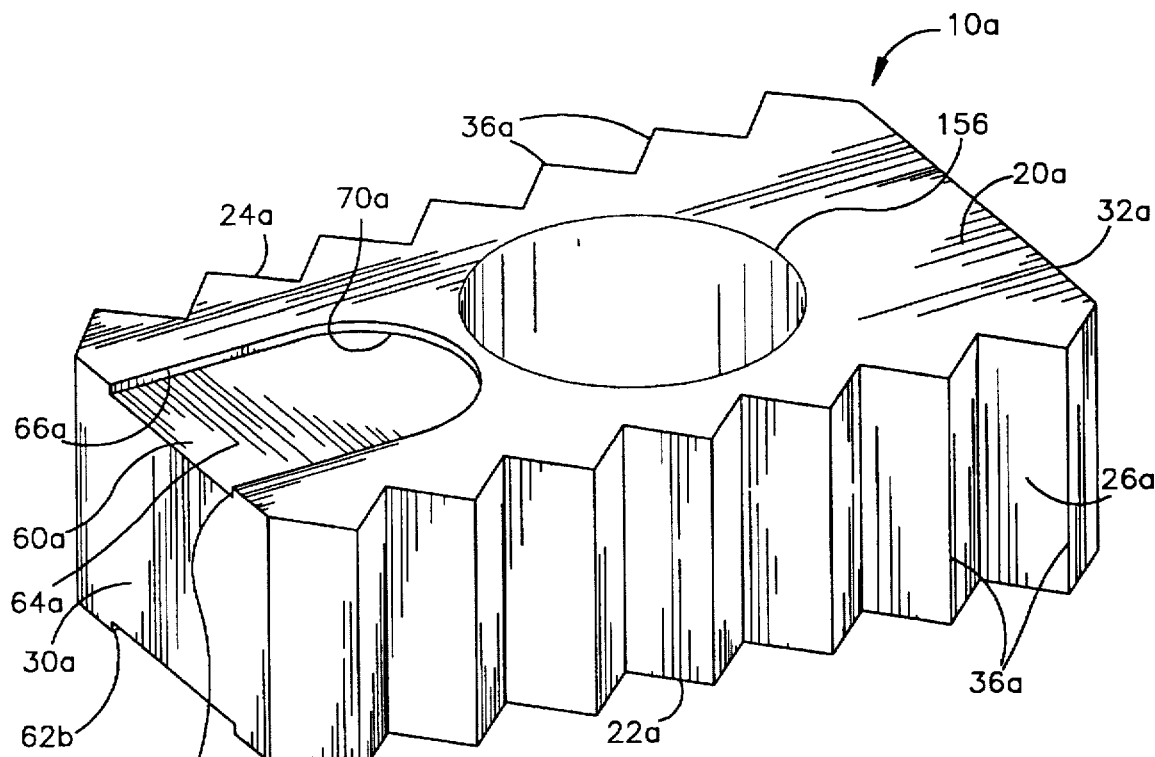
FIG. 13 is a perspective view of a second embodiment of a spinal implant of the present invention.
Figure 14:
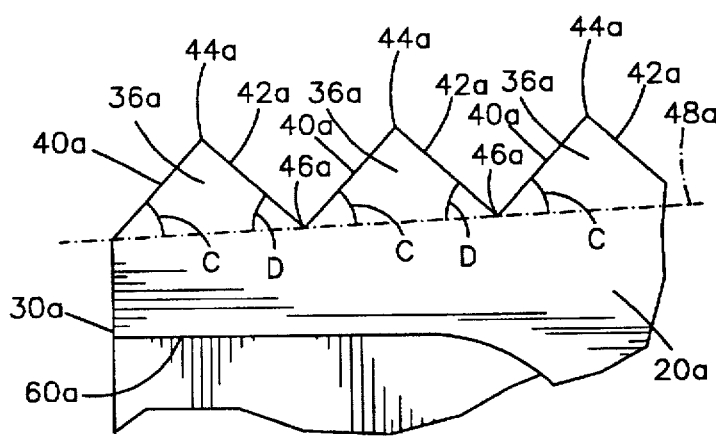
FIG. 14 is an enlarged plan view looking at a portion of the spinal implant of FIG. 13 from the side.

One or several substantially rigid spinal implants 10a (one of which is shown in FIG. 13) are placed between adjacent vertebrae of a spinal column in a side-by-side relationship to fuse together the adjacent vertebrae. Preferably, the spinal implants 10a are made by injection molding a chopped carbon fiber reinforced polymer. However, the spinal implants 10a can be made of other suitable implantable materials such as stainless steel or titanium. Also, preferably, the ultimate tensile strength of the material used to make the spinal implants 10a is higher than 10,000 psi so that the spinal implants will prevent relative movement between the adjacent vertebrae and will support the compressive load of the spinal column. Each of the spinal implants 10a (FIG. 13) has parallel side surfaces 20a and 22a. An upper surface 24a and a lower surface 26a for engaging the adjacent vertebrae extend between the side surfaces 20a and 22a. The upper and lower surfaces 24a and 26a adjacent a first end portion 30a of the spinal implant 10a are spaced apart by a first distance. The upper and lower surfaces 24a and 26a adjacent a second end portion 32a of the spinal implant 10a are spaced apart a second distance. The second distance is preferably greater than the first distance to give the spinal implant a wedge shape for use in portions of the spine with a lordotic curve. The spinal implant 10a may have a different wedge shape or no wedge shape depending on the portion of the spine into which the implant is to be inserted.

The upper and lower surfaces 24a and 26a include a plurality of triangular-shaped teeth 36a that extend from the side surface 20a to the side surface 22a for engaging the vertebrae. Each tooth 36a (FIG. 14) includes a surface 40a facing toward the end portion 30a. A surface 42a of each tooth 36a faces the end portion 32a of the spinal implant 10a. The surfaces 40a and 42a of the tooth 36a intersect each other to form an edge 44a. The surfaces 40a and 42a of adjacent teeth 36a intersect to form edges 46a. The edges 46a are parallel to each other and lie in a plane 48a.

The surface 40a of each tooth 36a extends at an acute angle C to the plane 48a. The surface 42a of each tooth 36a extends at an acute angle D to the plane 48a. Preferably, the angles C and D are equal and have a value of 45° so that surfaces 40a and 42a extend perpendicular to each other. Therefore, the teeth 36a are not preferential. However, the values of angles C and D may be different.

A relatively large opening 156 extends from the side surface 20a to the side surface 22a. The opening 156 is packed with autograft or allograft bone, bone proteins, bone substitute, or the like and provides for the flow of body fluids and bone growth from one side of the implant 10a to the other side of the implant. The opening 156 extends perpendicular to the side surfaces 20a and 22a and may extend at an angle to the side surfaces. The size, shape, and position of the opening 156 may be varied as desired by a surgeon.

The side surface 20a includes a recess 60a and the side surface 22a includes a recess 62a. Each of the recesses 60a and 62a includes a planar bottom surface 64a, parallel side surfaces 66a and 68a extending perpendicular to the bottom surface 64a, and an arcuate side surface 70a extending between the parallel side surfaces 66a and 68a. The recesses 60a and 62a in the side surfaces 20a and 22a are for receiving the instrument 80 (FIG. 4) that holds the spinal implant 10a to facilitate insertion of the spinal implant between the adjacent vertebrae and rotation of the spinal implant once between the adjacent vertebrae.

Any instrument that firmly holds the implant 10a and permits the implant to be rotated into position can be used. The instrument 80 is one such instrument that can be used.

The method of placing the spinal implants 10a between adjacent vertebrae to fuse together the adjacent vertebrae is similar to the method of placing the spinal implants 10 between adjacent vertebrae as shown in FIGS. 4–12 and therefore, will not be described in detail. Most of the spinal disc located between the vertebrae is removed. The facing surfaces of the vertebrae are cleaned with a disc shaver and rongeurs. Preferably, an annulus of the spinal disc is left between the vertebrae.

The opening 156 is packed with bone graft. The instrument 80 is used to hold a spinal implant 10a, as described in the embodiment of FIGS. 1–12. The spinal implant 10a is inserted posteriorly, anteriorly, or anterio-laterally between the vertebrae with the parallel side surfaces 20a and 22a facing the adjacent vertebrae. The spinal implant 10a is inserted so that the end portion 32a is near the anterior side of the spinal column and the end portion 30a is near the posterior side of the spinal column. The spinal implant 10a is rotated 90° so that the teeth 36a on the upper and lower surfaces 24a and 26a engage the vertebrae and the side surfaces 20a and 22a extend between the adjacent vertebrae.

A second spinal implant 10a is inserted between the vertebrae in a side-by-side relationship with the first spinal implant. The second spinal implant 10a is inserted in a similar manner as the first implant. The opening 156 is packed with bone graft. The instrument 80 is used to hold the spinal implant 10a. The spinal implant 10a is inserted with the parallel side surfaces 20a and 22a facing the vertebrae. The second spinal implant 10a is then rotated 90° so that the teeth 36a of the upper and lower surfaces 24a and 26a engage the vertebrae.

The remaining space between the spinal implants 10a and the adjacent vertebrae is packed with autograft or allograft bone, bone proteins, bone substitute, or the like. A suitable apparatus for maintaining the vertebrae in a desired spatial relationship is attached to the spinal column until the vertebrae have completely fused together.

In the embodiments of the invention illustrated in FIGS. 1–14, the spinal implants have openings extending between side surfaces only. In the embodiment of the invention illustrated in FIGS. 15 and 16, the spinal implant has an opening extending between side surfaces and an opening extending between upper and lower surfaces that engage adjacent vertebrae. Since the embodiment of the invention illustrated in FIGS. 15 and 16 is generally similar to the embodiments of the invention illustrated in FIGS. 1–14, similar numerals will be utilized to designate similar components, the suffix letter "b" being associated with the numerals of FIGS. 15 and 16 to avoid confusion.

Figure 15:
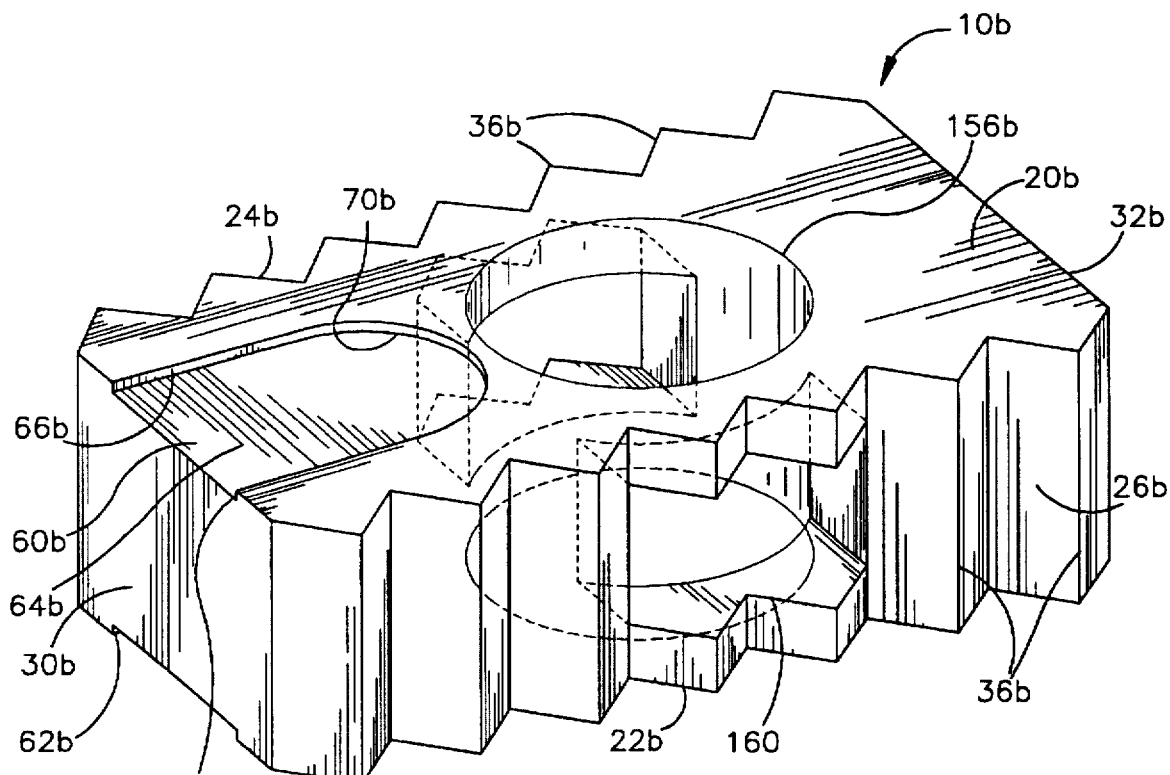
FIG. 15 is a perspective view of a third embodiment of a spinal implant of the present invention.
Figure 16:
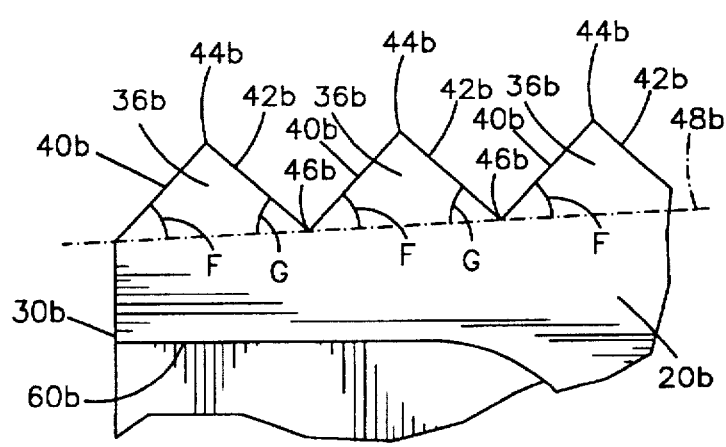
FIG. 16 is an enlarged plan view looking at a portion of the spinal implant of FIG. 15 from the side.

One or several substantially rigid spinal implants 10b (one of which is shown in FIG. 15) are placed between adjacent vertebrae of a spinal column in a side-by-side relationship to fuse together the adjacent vertebrae. Preferably, the spinal implants 10b are made by injection molding a chopped carbon fiber reinforced polymer. However, the spinal implants 10b can be made of other suitable implantable materials such as stainless steel or titanium. Also, preferably, the ultimate tensile strength of the material used to make the spinal implants 10b is higher than 10,000 psi so that the spinal implants will prevent relative movement between the adjacent vertebrae and will support the compressive load of the spinal column.

Each of the spinal implants 10b (FIG. 15) has parallel side surfaces 20b and 22b. An upper surface 24b and a lower surface 26b for engaging the adjacent vertebrae extend between the side surfaces 20b and 22b. The upper and lower surfaces 24b and 26b adjacent a first end portion 30b of the spinal implant 10b are spaced apart by a first distance. The upper and lower surfaces 24b and 26b adjacent a second end portion 32b of the spinal implant 10b are spaced apart a second distance. The second distance is preferably greater than the first distance to give the spinal implant a wedge shape for use in portions of the spine with a lordotic curve. The spinal implant 10b may have a different wedge shape or no wedge shape depending on the portion of the spine into which the implant is to be inserted.

The upper and lower surfaces 24b and 26b include a plurality of triangular-shaped teeth 36b that extend from the side surface 20b to the side surface 22b for engaging the vertebrae. Each tooth 36b (FIG. 16) includes a surface 40b facing toward the end portion 30b. A surface 42b of each tooth 36b faces the end portion 32b of the spinal implant 10b. The surfaces 40b and 42b of each tooth 36b intersect each other to form an edge 44b. The surfaces 40b and 42b of adjacent teeth 36b intersect to form edges 46b. The edges 46b are parallel to each other and lie in a plane 48b.

The surface 40b of each tooth 36b extends at an acute angle F to the plane 48b. The surface 42b of each tooth 36b extends at an acute angle G to the plane 48b. Preferably, the angles F and G are equal and have a value of 45° so that surfaces 40b and 42b extend perpendicular to each other. Therefore, the teeth 36b are not preferential. However, the values of angles F and G may be different.

A relatively large circular opening 156b extends from the side surface 20b to the side surface 22b. A relatively large rectangular opening 160 extends from the upper surface 24b to the lower surface 26b and intersects the opening 156b. The openings 156b and 160 are packed with autograft or allograft bone, bone proteins, bone substitute, or the like and provide for the flow of body fluids and bone growth through the implant 10b. The sizes, shapes, and positions of the openings 156b and 160 may be varied as desired by a surgeon.

The side surface 20b includes a recess 60b and the side surface 22b includes a recess 62b. Each of the recesses 60b and 62b includes a planar bottom surface 64b, parallel side surfaces 66b and 68b, and an arcuate side surface 70b extending between the parallel side surfaces 66b and 68b. The recesses 60b and 62b in the side surfaces 20b and 22b are for receiving the instrument 80 (FIG. 4) that holds the spinal implant 10b to facilitate insertion of the spinal implant between adjacent vertebrae and rotation of the spinal implant once between the adjacent vertebrae.

Any instrument that firmly holds the implant 10b and permits the implant to be rotated into position can be used. The instrument 80 is one such instrument that can be used.

The method of placing the spinal implants 10b between adjacent vertebrae to fuse together the adjacent vertebrae is similar to the method of placing the spinal implants 10 between adjacent vertebrae as shown in FIGS. 4–12 and will not be described in detail. Most of the spinal disc located between the vertebrae is removed. The facing surfaces of the vertebrae are cleaned with a disc shaver and rongeurs. Preferably, an annulus of the spinal disc is left between the vertebrae.

The openings 156b and 160 are packed with bone graft. The instrument 80 is used to hold a spinal implant 10b, as described in the embodiment of FIGS. 1–12. The spinal implant 10b is inserted posteriorly, anteriorly, or anteriolaterally between the vertebrae with the parallel side surfaces 20b and 22b facing the adjacent vertebrae. The spinal implant 10b is inserted so that the end portion 32b is near the anterior side of the spinal column and the end portion 30b is near the posterior side of the spinal column. The spinal implant 10b is rotated 90° so that the teeth 36b on the upper and lower surfaces 24b and 26b engage the vertebrae and the side surfaces 20b and 22b extend between the vertebrae.

A second spinal implant 10b is inserted between the vertebrae in a side-by-side relationship with the first spinal implant. The second spinal implant 10b is inserted in a similar manner as the first implant. The openings 156b and 160 are packed with bone graft. The instrument 80 is used to hold the spinal implant 10b. The spinal implant 10b is inserted with the parallel side surfaces 20b and 22b facing the vertebrae. The second spinal implant 10b is then rotated 90° so that the teeth 36b of the upper and lower surfaces 24b and 26b engage the vertebrae.

The remaining space between the spinal implants 10b and the adjacent vertebrae is packed with autograft or allograft bone, bone proteins, bone substitute, or the like. An apparatus for maintaining the vertebrae in a desired spatial relationship is attached to the spinal column until the vertebrae have completely fused together.

From the above description of the invention, those skilled in the art will perceive improvements, changes and modifications. Such improvements, changes and modifications within the skill of the art are intended to be covered by the appended claims.

Having described the invention, the following is claimed:

1. A spinal implant for use in fusing together adjacent vertebrae of a spinal column comprising:

first and second side surfaces extending substantially parallel to each other;

upper and lower surface means for engaging the adjacent vertebrae extending between said first and second side surfaces, said spinal implant having a first position between the adjacent vertebrae in which said first and second side surfaces face the adjacent vertebrae and a second position in which said upper and lower surface means engage the adjacent vertebrae and said first and second side surfaces extend from one of the adjacent vertebrae to another of the adjacent vertebrae;

first and second end portions; and means for engaging a tool for rotation of said spinal implant from said first position in which said first and second side surfaces face the adjacent vertebrae to said second position in which said upper and lower surface means engage the adjacent vertebrae, said tool engaging means including first and second surface means on said first and second side surfaces, respectively, for engaging the tool, said first and second surface means including means for enabling rotation of said spinal implant from said first position to said second position.

2. A spinal implant as set forth in claim 1 wherein said upper and lower surface means extend from said first end portion to said second end portion, said upper and lower surface means adjacent said first end portion being spaced apart by a first distance and said upper and lower surface means adjacent said second end portion being spaced apart by a second distance greater than the first distance.

3. A spinal implant as set forth in claim 1 further including at least one opening extending through said spinal implant.

4. A spinal implant as set forth in claim 3 wherein said opening extends from said upper surface means to said lower surface means.

5. A spinal implant as set forth in claim 3 wherein said opening extends from said first side surface to said second side surface.

6. A spinal implant as set forth in claim 5 further including a plurality of openings extending from said first side surface to said second side surface.

7. A spinal implant as set forth in claim 6 wherein said openings extend substantially perpendicular to said first and second side surfaces.

8. A spinal implant as set forth in claim 5 further including an opening extending from said upper surface means to said lower surface means.

9. A spinal implant as set forth in claim 8 wherein said opening extending from said upper surface means to said lower surface means intersects said opening extending from said first side surface to said second side surface.

10. A spinal implant as set forth in claim 1 wherein said upper and lower surface means include teeth for engaging the adjacent vertebrae.

11. A spinal implant as set forth in claim 10 wherein said teeth on said upper and lower surface means are triangular shaped.

12. A spinal implant as set forth in claim 11 wherein each of said teeth includes a first surface facing toward said first end portion and a second surface extending from said first surface of said tooth and facing said second end portion, said first and second surfaces of said tooth intersecting each other to form an edge, said first surface extending at an acute angle to a plane containing an edge of said first surface opposite from said edge defined by the intersection of said first and second surfaces and containing an edge of said second surface opposite from said edge defined by the intersection of said first and second surfaces, said second surface extending at an acute angle to the plane equal to the acute angle that said first surface extends from said plane.

13. A spinal implant as set forth in claim 12 wherein said first surface extends perpendicular to said second surface.

14. A spinal implant as set forth in claim 1 wherein said means for engaging a tool comprises recesses in said first and second side surfaces for receiving the tool for grasping and rotating said spinal implant.

15. A spinal implant as set forth in claim 2 wherein said means for engaging a tool comprises recesses located adjacent said first end portion of said spinal implant.

16. A spinal implant for use in fusing together adjacent vertebrae of a spinal column comprising:

first and second side surface means for extending from one of the adjacent vertebrae to the other of the adjacent vertebrae, said first and second side surface means being spaced apart a first distance;

upper and lower surface means for engaging the adjacent vertebrae extending between said first and second side surface means, said upper and lower surface means being spaced apart a second distance greater than the first distance; and first and second end portions;

said spinal implant having a first position between the adjacent vertebrae in which said first and second side surface means face the adjacent vertebrae and a second position in which said upper and lower surface means engage the adjacent vertebrae and said first and second side surface means extend from one of the adjacent vertebrae to another of the adjacent vertebrae, said spinal implant being rotatable about an axis extending through said first and second end portions from said first position in which said first and second side surface means face the adjacent vertebrae to said second position in which said upper and lower surface means engage the adjacent vertebrae and said first and second side surface means extend from one of the adjacent vertebrae to another of the adjacent vertebrae; and first and second tool engaging surface means located on said first and second side surface means, respectively, for engaging a tool for rotating said spinal implant, said first and second tool engaging means including means for enabling rotation of said spinal implant from said first position to said second position.

17. A spinal implant as set forth in claim 16 wherein said first and second side surface means extend substantially parallel to each other.

18. A spinal implant as set forth in claim 16 wherein said upper and lower surface means extend from said first end portion to said second end portion, said upper and lower surface means adjacent said first end portion being spaced apart by a third distance and said upper and lower surface means adjacent said second end portion being spaced apart by a fourth distance greater than the third distance.

19. A spinal implant as set forth in claim 16 further including at least one opening extending through said spinal implant.

20. A spinal implant as set forth in claim 16 wherein said upper and lower surface means include teeth for engaging the adjacent vertebrae.

21. A spinal implant as set forth in claim 20 wherein each of said teeth includes a first surface facing toward said first end portion and a second surface extending from said first surface of said tooth and facing said second end portion, said first and second surfaces of said tooth intersecting each other to form an edge, said first surface extending at an acute angle to a plane containing an edge of said first surface opposite from said edge defined by the intersection of said first and second surfaces and containing an edge of said second surface opposite from said edge defined by the intersection of said first and second surfaces, said second surface extending at an acute angle to the plane equal to the acute angle that said first surface extends from said plane.

* * * * *